United States Patent [19]

Meador et al.

[11] Patent Number: 4,458,524
[45] Date of Patent: Jul. 10, 1984

[54] CRUDE OIL PRODUCTION STREAM ANALYZER

[75] Inventors: Richard A. Meador, Spring; Hans J. Paap, Houston, both of Tex.

[73] Assignee: Texaco Inc., White Plains, N.Y.

[21] Appl. No.: 335,304

[22] Filed: Dec. 28, 1981

[51] Int. Cl.³ .......................................... G01N 33/22
[52] U.S. Cl. .................................. 73/61.1 R; 374/101
[58] Field of Search .............. 73/61 R, 61.1 R, 53; 324/204, 227, 225, 306, 61 R; 378/53, 57; 374/101

[56] References Cited

U.S. PATENT DOCUMENTS

| | | | |
|---|---|---|---|
| 3,191,119 | 6/1965 | Singer | 324/306 |
| 3,253,606 | 5/1966 | Kuntz | 324/61 R X |
| 3,335,364 | 8/1967 | Lode | 324/61 R |
| 3,774,237 | 11/1973 | Hardway, Jr. | 73/61.1 R X |
| 3,815,021 | 6/1974 | Kerr | 324/61 R |
| 4,352,288 | 10/1982 | Paap et al. | 73/61 R |
| 4,364,262 | 12/1982 | Woodle et al. | 73/53 |

Primary Examiner—S. Clement Swisher
Assistant Examiner—Brian R. Tumm
Attorney, Agent, or Firm—Robert A. Kulason; Carl G. Ries; Ronald G. Gillespie

[57] ABSTRACT

A crude oil production stream analyzer includes a device which measures the dielectric constant of the crude oil production stream and provides a signal corresponding thereto. A densitometer provides a density signal representative of the density of the crude oil production stream. At least one constituent of the crude oil production stream is determined in accordance with the dielectric constant signal and the density signal and the temperature of the crude oil production stream which is sensed by a temperature sensor.

14 Claims, 6 Drawing Figures

CRUDE OIL PRODUCTION STREAM ANALYZER

BACKGROUND OF THE INVENTION

FIELD OF THE INVENTION

The present invention relates to oil industry monitors in general and, more particularly, to water-in-crude monitors.

SUMMARY OF THE INVENTION

A crude oil production stream analyzer includes devices, apparatus and a sensor which measures the dielectric constant, the density and the temperature of the crude oil production stream, respectively. The quantity of at least one constituent of the crude oil production stream is determined in accordance with the measured dielectric constant, density and temperature.

The objects and advantages of the invention will appear more fully hereinafter from a consideration of the detailed description which follows, taken together with the accompanying drawings wherein two embodiments of the invention are illustrated by way of example. It is to be expressly understood, however, that the drawings are for illustration purposes only and are not to be construed as defining the limits of the invention.

DESCRIPTION OF THE INVENTION

THEORY

Production streams in the recovery of crude oil from an earth formation generally are not 100% crude oil but contain in various degrees water (or brine) or gas. The present invention has discovered a relationship among characteristics of a crude oil production stream that allows the determination of the quantities of those production stream constituents.

Theoretical calculations using plane wave theory indicate that the dielectric constant of a material may be measured by measuring the phase difference between the signals received at two separated points from a common source. This phase shift is representative of the wave travel time between the two points. Mathematically, $$\Delta\theta = (d\sqrt{\epsilon}/\lambda_{air})(360) \tag{1}$$

where d is the distance between the points, $\lambda_{air}$ is the wavelength in air and $\epsilon$ is the dielectric constant of the material. Rearranging, $$\epsilon = [(\Delta\theta)(\lambda_{air})/((d)(360))]^2. \tag{2}$$

Figure 1:
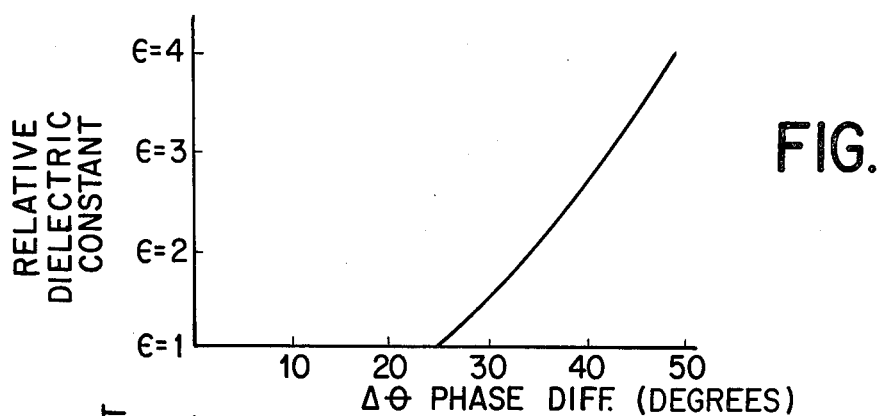
FIGS. 1, 2, 3 and 4 are plots of "relative dielectric constant" versus "$\Delta\theta$ phase difference," "dielectric constant" versus "$V_g$" fractional volume of gas, "phase difference" versus "$V_g$" and "$\epsilon w$" dielectric constant of water versus "temperature," respectively.

The phase difference measurement for a given dielectric constant is shown in FIG. 1. This chart is constructed based on plane wave theory, for a frequency of 200 MHz and a spacing of 4 inches between coils in a device of the present invention as hereinafter described.

Figure 2:
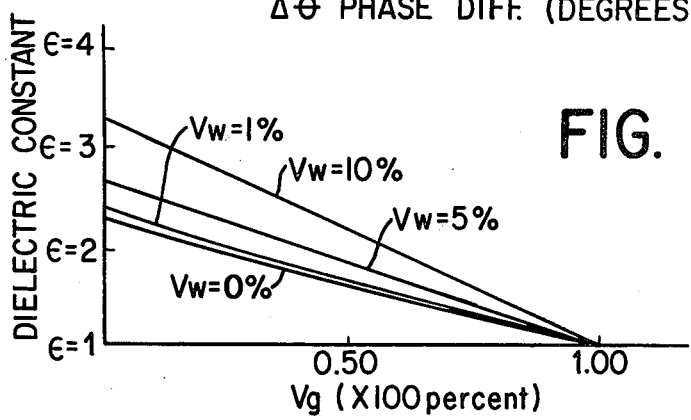

The influence of gas and water on the dielectric constant is shown in FIG. 2. This again is based on theoretical plane wave theory. Also, the assumption has been generally made that the oil is in the continuous phase.

Figure 3:
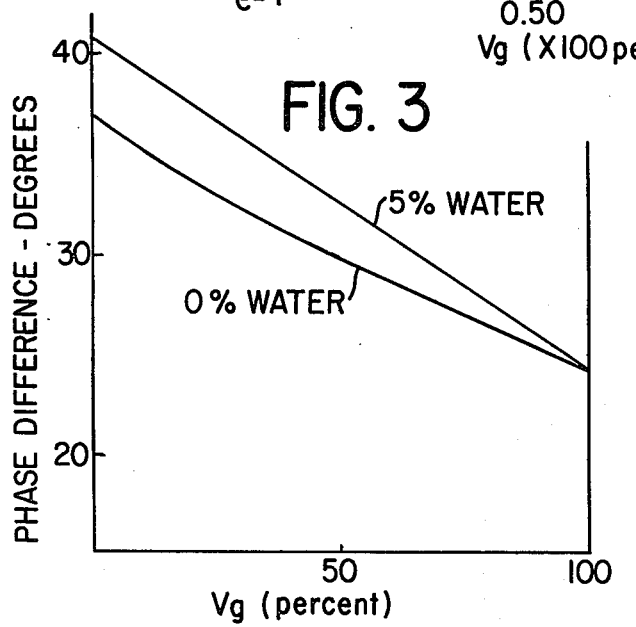
Figure 4:
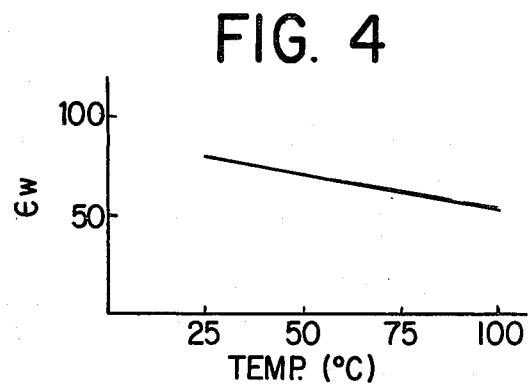

Inserting the data of FIG. 2 into the system measurement characteristics of FIG. 1 yields the curve shown in FIG. 3. FIG. 4 shows the effect of temperature on the dielectric constant of water.

FIG. 1 is a plot of the relative dielectric constant vs. phase difference in degrees while FIG. 2 is a plot of the following equation $$\ln \epsilon_m = V_o \ln \epsilon_o + V_w \ln \epsilon_w \tag{3}$$

where $V_o$ is the volume fraction of oil, $V_w$ is the volume fraction of water, $\epsilon_m$ is the measured dielectric constant of the production stream, $\epsilon_o$ is the relative dielectric constant of oil and $\epsilon_w$ is the relative dielectric constant of water.

Relating the dielectric constant to the volume fraction of gas, FIG. 3 is a plot of phase difference in degrees vs. volume fraction of gas.

The determination of $V_g$ involves the following relationship $$V_g = 1 - V_L. \tag{4}$$

The density, which is related to the constituent volumes of the production stream as hereinafter described, is determined with a gamma ray density gauge which irradiates the production stream with gamma radiation. The gamma radiation, after passing through the production stream, is detected and a count rate C is developed. The count rate C is related to the measured density $\rho_m$ in the following equation $$\rho_m = K \ln (C_0/C) \tag{5}$$

where K and $C_0$ are calibration constants which are predetermined. Density $\rho_m$ is related to the densities of the different constituents of the production stream as shown in the following equation $$\rho_m = V_g\rho_g + V_o\rho_o + V_w\rho_w \tag{6}$$

where $V_g$, $V_o$, $V_w$, $\rho_g$, $\rho_o$ and $\rho_w$ are the volume fractions and densities of the gas, oil and water phases of the production stream, respectively. A volume $V_L$, the liquid phase fraction of the fluid, is given by the following equation $$V_L = V_o + V_w, \ \rho_L = (V_o\rho_o + V_w\rho_w)/V_L \tag{7}$$

so that equation (6) may be rewritten as $$\rho_m = V_g\rho_g + V_L\rho_L. \tag{8}$$

It should be noted that $\rho_g << \rho_L$ and that equation (8) may be written as an approximation $$\rho_m \approx V_L\rho_L \tag{9}$$

and hence $$V_L = (\rho_m/\rho_L). \tag{10}$$

When in equation 6 and 8, the term $V_g\rho_g$ is not negligible the gas density $\rho_g$ can be determined from temperature and pressure and pressure-volume-temperature (PVT) data for the particular oil-gas system according to well known techniques.

With the densities $\rho_o$, $\rho_w$ and $\rho_g$ and dielectric constants of $\epsilon_o$ and $\epsilon_w$ known there are three equations with three unknown variables $V_g$, $V_o$, and $V_w$ as follows:

$$\ln \epsilon_m = V_o \ln \epsilon_o + V_w \ln \epsilon_w \tag{11}$$

$$1 = V_o + V_w + V_g \tag{12}$$

$$\rho_m = V_g\rho_g + V_w\rho_w + V_o\rho_o \tag{13}$$

The variables can be determined from equations 11-13, $\epsilon_m$ and $\rho_m$ are measured.

Thus, knowing the dielectric constants and densities for oil and water and measuring the dielectric constant, temperature and density of the production stream, the water volume fraction can be determined. Further if the water phase is brine, the salinity of the brine may be measured separately and the salt content may then be determined from $V_w$ and the salinity if so desired. When the gas pressure is not negligible, the water volume fraction can still be determined by measuring the pressure of the production stream and the water volume fraction is determined accordingly.

WATER-IN-CRUDE MONITOR

Figure 5:
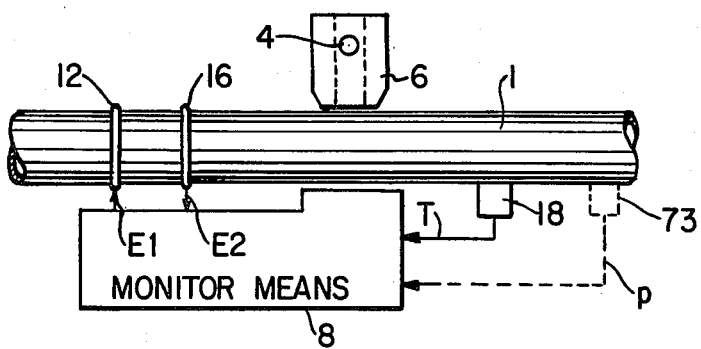
FIG. 5 is a simplified block diagram of a water-in-crude monitor constructed in accordance with the present invention.

The foregoing theory shows the interrelationship of the different constituents of the crude oil production stream. Those equations are all well known in the art and are part of the public domain. The present invention utilizes the novel relationship between those equations and does so without actually using the equations. With reference to FIG. 5, the production stream, consisting of various phases of crude oil, water and gas, flows through a pipe 1 a portion of which is non-conductive and non-magnetic. A $Cs^{137}$ gamma ray source 4 is mounted within a lead collimator 6 and irradiates the production stream in pipe 1 with gamma radiation.

Monitor means 8 receives the gamma radiation after passage through the production stream. Monitor means 8 also provides an electrical VHF or UHF signal E1, preferably at a frequency of 200 MHz, to a transmitting coil 12 encircling the non-conductive, non-magnetic portion of pipe 1 so as to develop electromagnetic energy within the production stream. A receiver coil 16, spaced a predetermined distance from coil 12 and also encircling non-conductive, non-magnetic portion of pipe 1, provides a signal E2, at substantially the same frequency as signal E1, to monitor means 8 in accordance with received electromagnetic energy from the production stream. A temperature sensor 18 senses the temperature of the production stream and provides a corresponding signal T to monitor means 8. Monitor means 8 provides an indication of the water content of the production stream in accordance with the received signals E2 and T and the received gamma radiation as hereinafter explained.

Figure 6:
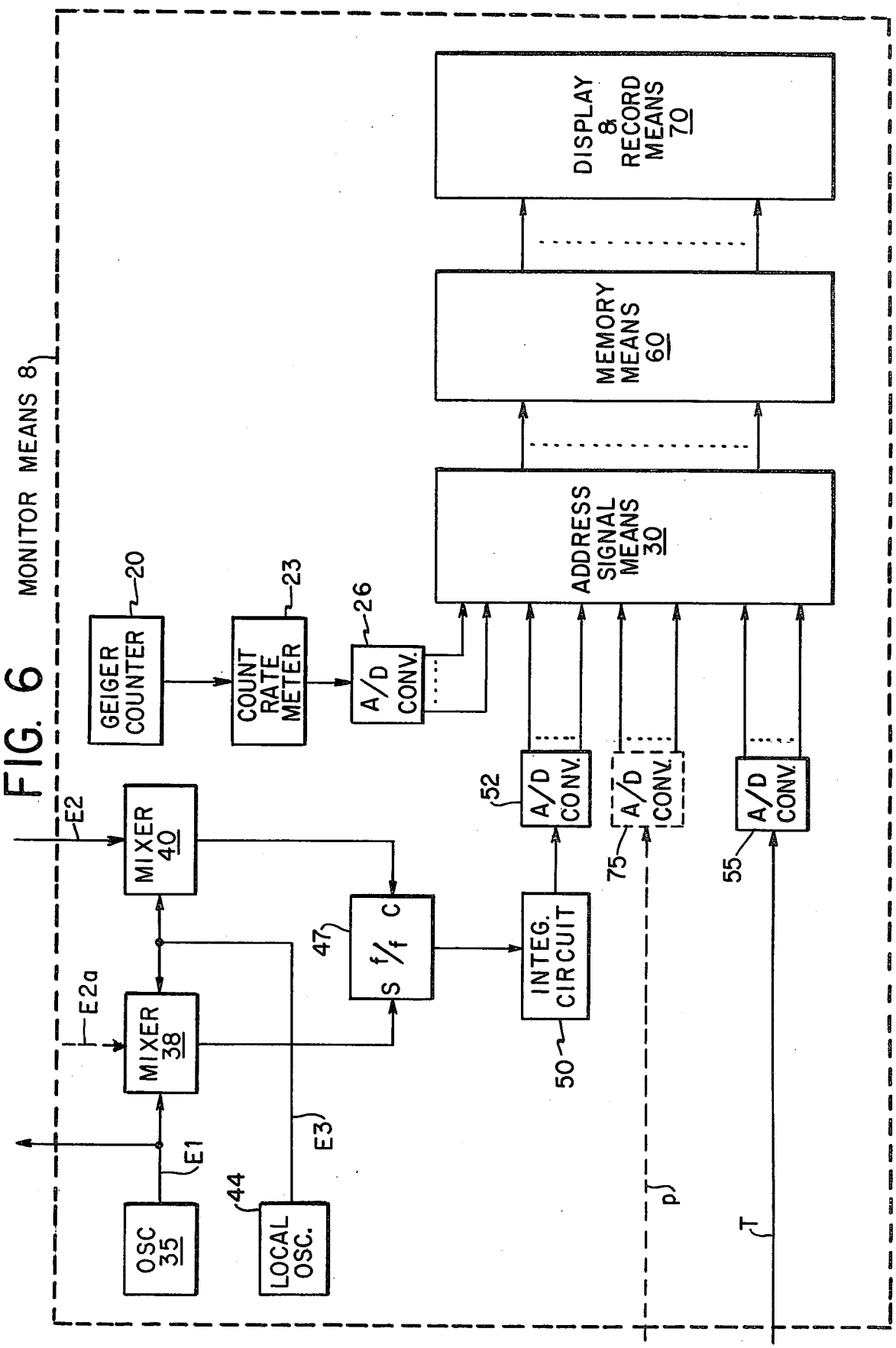
FIG. 6 is a detailed block diagram of the monitor means shown in FIG. 5.

Referring now to FIG. 6, a geiger counter 20 provides pulses in accordance with the gamma radiation that has passed through the production stream. A count rate meter 23 receives the pulses from geiger counter 20 and provides a signal corresponding to the count rate of the pulses from geiger counter 23 and hence to the detected gamma radiation. The count rate signal from the meter 23 is converted to digital signals by an analog-to-digital converter 26 which provides the digital signals to address signal means 30.

An oscillator 35 provides signal E1, which preferably is at a frequency of 200 MHz, to transmitter coil 12 and also to a mixer 38. Signal E2 from coil 16 is provided to another mixer 40. Mixers 38 and 40 receive a signal E3 from a local oscillator 44. Mixers 38 and 40 provide signals to a flip-flop 47 in accordance with the transmitted signals E1, the received signals E2 and the local oscillator frequency signal E3 with a frequency slightly different from that of oscillator 35 and preferably at a frequency of 199.998 MHz. The output from flip-flop 47 is provided to an integrating circuit 50 which provides an analog, signal corresponding to the phase difference and hence the phase shift due to the dielectric constant of the production stream. The signal from integrating circuit 50 is provided to another analog-to-digital converter 52 which provides corresponding digital signals to address signal means 30.

Signal T from temperature sensor 18 is converted to digital signals by an analog-to-digital converter 55 which provides the digital signals to address signal means 30.

Address signal means 30 provides memory address signals to memory means 60 to select information stored in memory means 60. Different volumes, in digital form, of constituents of the production stream are stored in memory means 60. In the present example, for each combination of temperature, measured phase shift and detected gamma radiation there is stored a corresponding value for $V_w$, as determined by prior calibration. The address signals cause memory means 60 to select the appropriate water fractional volume of the production stream and provide signals to display means 70 for display. Of course, it would be obvious to one skilled in the art that the gas and crude oil fractional volumes may also be stored. If the water is brine then the salt content may be stored in lieu of the fractional water volume value if so desired.

In another embodiment, which is so minor in description as not to warrant a separate figure, a second receiver coil providing a signal E2a, corresponding to received electromagnetic energy from the production stream, may be used in the determination of the phase shift. With reference to FIGS. 5 and 6, the two receiver coils are spaced a predetermined distance apart. Signal E1 is not provided to mixer 38, but mixer 38 now receives signal E2a indicated by the dashed line. The monitor then operates as previously described in the first embodiment of the present invention.

In yet another embodiment, when the gas density is not negligible, the present invention may be modified by using a pressure sensor 73 to sense the pressure of the production stream. Sensor 73 would then provide a corresponding analog pressure signal p to monitor means 8. In monitor means 8, signal p would be converted to digital signals by an analog-to-digital converter 75 and applied to address signal means 30. Of course, memory means 60 would have to have the gas density data stored within it and controlled to select the proper $\rho_g$. However, due to the complexity now encountered, it may be more desirable to use a computer to solve operations (11) through (13) to determine the water volume fraction.

The crude oil production stream analyzer as hereinbefore described determines the water cut of a production stream in accordance with the density, the dielectric constant and the temperature of the production stream.

What is claimed is:

1. A production stream analyzer for use with a flowing crude oil production stream, said stream having other constituents besides crude oil, comprises:
    an electrically non-conductive and non-magnetic conduit through which the production stream flows,
    a sensor sensing the temperature of the flowing production stream and providing a temperature signal representative thereof,
    means for transmitting electromagnetic energy into the production stream,
    means for receiving electromagnetic energy from the production stream at a predetermined location from said transmitting means,
    means for determining the dielectric constant of the production stream in accordance with the transmitted electromagnetic energy and the received electromagnetic energy and providing a corresponding dielectric constant signal,
    a densitometer meausuring the density of the production stream and providing a density signal corresponding thereto, and
    output means for providing output signals corresponding to the quantity of at least one constituent of the production stream in accordance with the temperaure signal, the dielectric constant signal and the density signal.

2. An analyzer as described in claim 1 in which the transmitting means includes:
    transmitter coil means encircling said conduit for transmitting electromagnetic energy into the production stream in response to an energizing voltage at a predetermined frequency, and
    means connected to the transmitting coil means for providing the energizing voltage to the transmitting coil means so as to energize the transmitting coil means;
    the receiving means includes:
    receiver coil means spaced a predetermined distance from said transmitting coil means for providing a signal corresponding to received electromagnetic energy from the production stream; and
    the dielectric constant determining means includes:
    means connected to the energizing means and to the receiver coil means for determining the phase difference between the energizer voltage and the signal provided by the receiver coil means and providing a corresponding phase difference signal, and
    means connected to the phase difference means for providing the signal corresponding to the dielectric constant of the production stream in accordance with the phase difference signal from the phase difference means.

3. An analyzer as described in claim 2 in which the densitometer includes
    means for irradiating the production stream with gamma radiation in a manner so that the gamma radiation passes through the production stream, and
    means responsive to the gamma radiation that has passed through the production stream for providing the density signal corresponding to the density of the production stream.

4. An analyzer as described in claim 3 in which the output means includes:
    means for providing address signals in accordance with the density signal, the dielectric constant signal and the temperature signal, and
    memory means having stored within it different values of fractional volumes of the constituent of the production stream for selecting a stored value in accordance with the address signals and for providing signals corresponding to the selected stored value of the constituent as the output signals; and further comprising
    recording means connected to the memory means for recording the output signals.

5. An analyzer as described in claim 4 further comprising
    means connected to the address signal means for sensing the pressure of the production stream and for providing a corresponding pressure signal to the address signal means; and
    in which the address signal means provides the address signals in accordance with the density signal, the pressure signal, the dielectric constant signal and the temperature signal.

6. An analyzer as described in claim 4 or claim 5 in which the radiation responsive means includes
    a geiger counter responsive to the radiation that has passed through the production stream provides pulses in accordance with the detected gamma radiation, and
    a count rate meter connected to the geiger counter provides a signal corresponding to the count rate of the pulses from the geiger counter as the density signal.

7. An analyzer as described in claim 6 in which the energizing means is an energizing oscillator and the phase difference means includes
    a local oscillator providing a signal at a second predetermined frequency,
    a first mixer connected to the oscillator and to the local oscillator for providing a signal in accordance with the signals from both oscillators,
    a second mixer connected to the local oscillator and to the receiver coil for providing a signal in accordance with the signal from the local oscillator and the signal from the receiving coil means,
    a flip-flop connected to both mixers provides an output signal whose time duration at one amplitude corresponds to the time differential between the electromagnetic energy transmitted by the transmitting coil means and the electromagnetic energy received by the receiver coil means, and
    an integrating circuit connected to the flip-flop integrates the output signal from the flip-flop to provide the phase difference signal.

8. An analyzer as described in claim 6 further comprising:
    a second receiver coil means located a predetermined distance from the first mentioned receiver coil means for receiving the transmitted electromagnetic energy from the production stream and providing a corresponding signal; and
    in which energizing means is an energizing oscillator, and
    the phase difference means includes:
    a local oscillator providing a signal at a second predetermined frequency, a first mixer connected to the first mentioned receiver coil means and to the local oscillator which provides a signal in accordance with the signals from the first receiver coil means and the local oscillator, a second mixer connected to the local oscillator and to the second receiver coil means for providing a signal in accordance with the signal from the local oscillator and the signal from the second receiving coil means, a flip-flop connected to both mixers provides an output signal whose time duration at one amplitude corresponds to the time differential between the electromagnetic energy received by the first mentioned receiver coil means and the electromagnetic energy received by the second receiver coil means, and an integrating circuit connected to the flip-flop integrates the output signal from the flip-flop to provide the phase difference signal.

9. An analyzer as described in claim 8 in which the predetermined distance is four inches.

10. An analyzer as described in claim 9 in which the means for irradiating the production stream with gamma radiation includes a $Cs^{137}$ gamma ray source.

11. A method of analyzing a flowing crude oil production stream in an electrically non-conductive, non-magnetic conduit, said stream having other constituents besides crude oil, which comprises the steps of:

sensing the temperature of the production stream and providing a corresponding temperature signal, transmitting electromagnetic energy into the production stream, receiving electromagnetic energy from the production stream at a location downstream from where the electromagnetic energy was transmitted into the production stream, determining the dielectric constant of the production stream in accordance with the transmitted electromagnetic energy and the received electromagnetic energy, measuring the density of the production stream, and determining the quantity of at least one constituent of the production stream in accordance with the sensed temperature, the determined dielectric constant and the measured density.

12. A method as described in claim 11 in which the transmitting step includes:

energizing a transmitting coil with an energizing voltage having a predetermined frequency;

the receiving step includes:

receiving electromagnetic energy from the production stream at a predetermined distance from the transmitting coil; and the dielectric constant determining step includes:

determining the phase difference between the energizing voltage and the received electromagnetic energy, and providing a signal corresponding to the dielectric constant of the production stream in accordance with the determined phase difference.

13. A method as described in claim 12 in which the density measuring step includes:

irradiating the production stream with gamma radiation in a manner so that the gamma radiation passes through the production stream, providing a density signal corresponding to the density of the production stream in accordance with the gamma radiation that has passed through the production stream; and further comprising:

storing values of fractional volumes of the constituent of the production stream, selecting a stored value in accordance with the density signal, the dielectric constant signal and the temperature signal, and providing signals corresponding to the selected value as the output signals, and recording the output signals.

14. A method as described in claim 13 in which the density signal step includes receiving the radiation that has passed through the production stream with a geiger counter, providing pulses in accordance with the received gamma radiation, counting the pulses, and providing the density signal in accordance with the count rate of the pulses.

* * * * *